United States Patent [19]  
Lichfield

[11] 4,304,245  
[45] Dec. 8, 1981

[54] THERAPEUTIC TOOTHPICK

[76] Inventor: William H. Lichfield, Box 112, Corinne, Utah 84307

[21] Appl. No.: 160,083

[22] Filed: Jun. 16, 1980

[51] Int. Cl.³ .............................................. A61C 15/00
[52] U.S. Cl. ...................................................... 132/89
[58] Field of Search ....................... 132/89, 90, 91, 92, 132/93

[56] References Cited

U.S. PATENT DOCUMENTS 2,771,085 11/1956 Fleming .................................. 132/89
3,913,596 10/1975 Stuart .................................... 132/89

FOREIGN PATENT DOCUMENTS 268022 6/1912 Fed. Rep. of Germany ........ 132/89
8803 of 1908 United Kingdom .................. 132/89

Primary Examiner—Robert A. Hafer

[57] ABSTRACT

A toothpick for cleaning teeth and for gingival stimulation consists of a four-sided sheet of thin polymeric material curled back upon itself to form a hollow body having a forwardly tapering layered front end with spiraling ridges and either an enlarged central and rear portion or an enlarged central portion and a backwardly tapered layered rear end portion.

17 Claims, 20 Drawing Figures

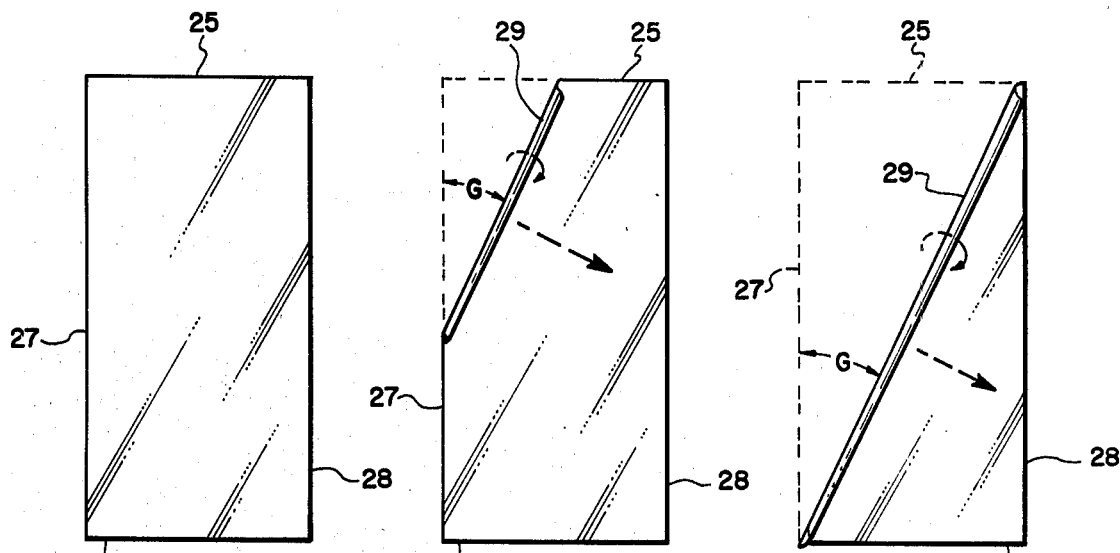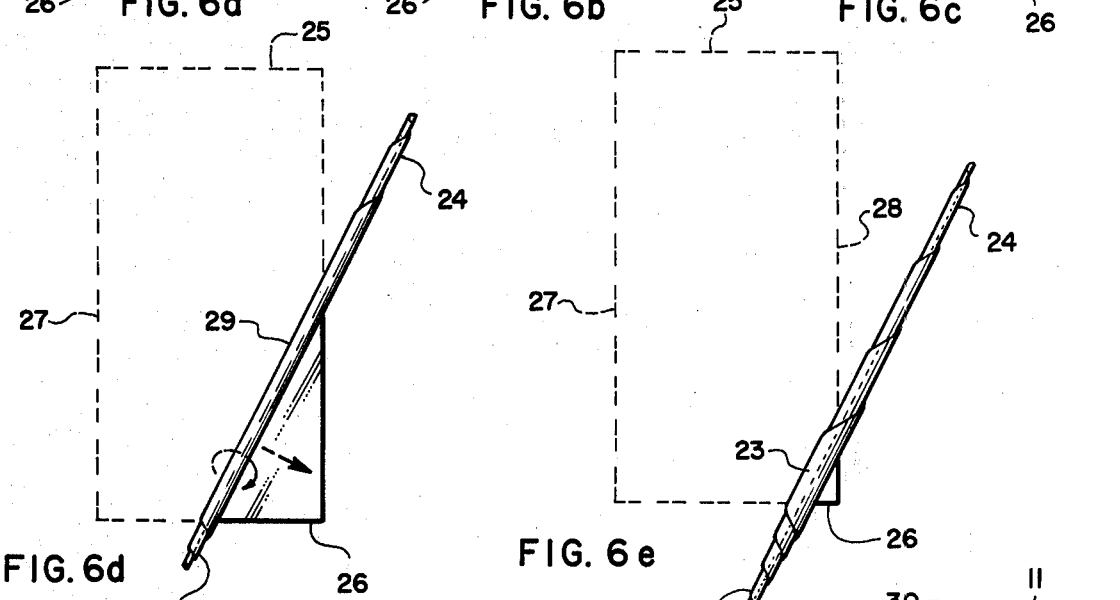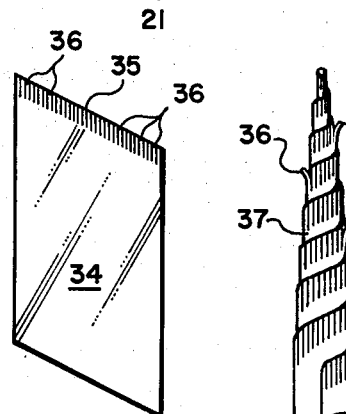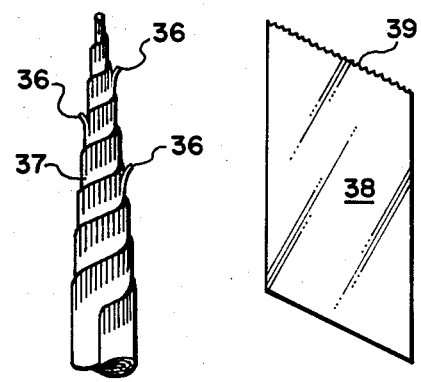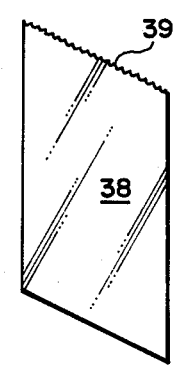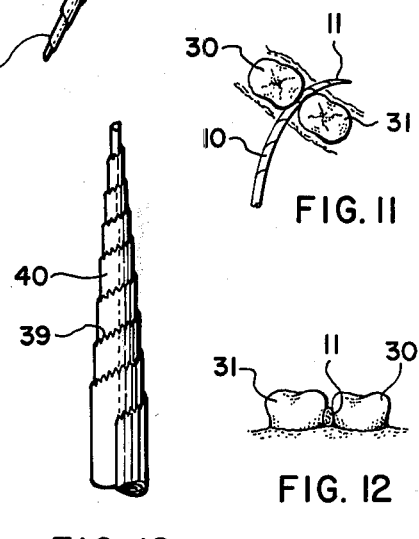

THERAPEUTIC TOOTHPICK

BACKGROUND OF THE INVENTION

This invention relates to a therapeutic appliance for the use in oral hygiene. More particularly this invention relates to a layered pliable toothpick for cleaning teeth and stimulating gingival surfaces.

Generally speaking, a toothpick is a pointed instrument used for removing food or other particles from between the teeth. Such instruments are tapered to a point at one or both ends and are made of a solid piece of material such as wood or plastic. Constructed as such, they are limited to the specific use of dislodging particles from the teeth which can be conveniently reached due to the rigidity of the toothpick and can be dangerous if improperly or negligently used. For example, a small child may fall with a toothpick in his mouth and severely damage his mouth because the toothpick is sharp and rigid. Because of its rigidity, a conventional toothpick is damaging to soft tissues and is limited in the areas it can reach and extend into. It is therefore of little value in gum massage or stimulation.

OBJECTS AND SUMMARY OF THE INVENTION

It is an object of the present invention to provide a therapeutic tooth appliance that is rigid enough to remove particles from between teeth but is pliable enough to clean and stimulate gingival surfaces.

It is also an object of this invention to provide a tooth cleaning appliance that will not penetrate or damage the inner surfaces of the oral cavity should the appliance be suddenly forced into the mouth by external forces.

Another object of the invention is to provide a tooth cleaning appliance that will supply a medicine, disinfectant or breath freshener to the oral cavity or remove undesirable fluids from within the oral cavity.

A still further object of this invention is to provide a flexible tooth cleaning appliance that is suitable for pontic cleaning and for removing plaque from interproximal areas of the teeth.

These and other objects may be accomplished by means of a toothpick shaped appliance consisting of a thin, oblong or parallelogram sheet of flexible polymeric material which is tightly rolled or curled back upon itself in a direction which results in a layered toothpick having a hollow, forwardly tapering, front end, an enlarged central portion and a back end which may or may not be tapered. Medicaments, disinfectants, breath sweeteners or other materials may be placed in the hollow core.

DRAWINGS OF THE INVENTION

FIGS. 6a to 6e are a sequential illustration of a sheet of plastic being rolled to form the toothpick of FIG. 2.

FIG. 7 is a view of a sheet of plastic as shown in FIG. 5a wherein the top edge has been scored.

FIG. 8 is a perspective view of a toothpick formed from the plastic shown in FIG. 7.

FIG. 9 is a view of a sheet of plastic as shown in FIG. 5a wherein the top edge has been serrated.

FIG. 10 is a perspective view of a toothpick formed from the plastic shown in FIG. 9.

FIG. 11 is a partial top view of a users teeth showing how the toothpicks of the invention bend to conform to the angle and contour of the crevice between the teeth.

FIG. 12 is a partial back view of a users teeth with a toothpick protruding between the teeth showing how the toothpick of the invention may be deformed to assume the shape of the crevice between the teeth.

DETAILED DESCRIPTION OF THE INVENTION

Various complete embodiments of the invention are illustrated in FIGS. 1, 2, 8 and 9 with supporting figures showing how such toothpicks may be formed and used.

A preferred embodiment of the invention is shown in FIGS. 1, 3, 4 and 5a to 5e.

Figure 1:
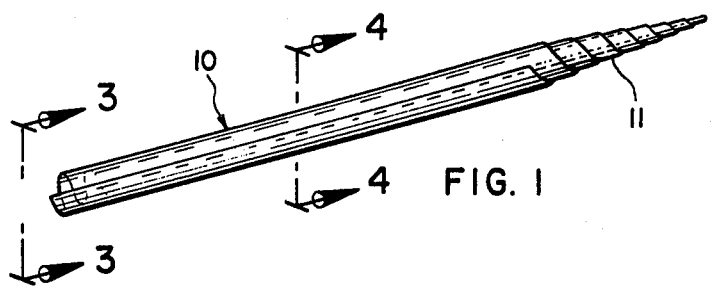
FIG. 1 is an enlarged perspective view of one embodiment of a layered toothpick having a tapered front end.

FIG. 1 shows a toothpick 10 having a spirally layered forwardly tapered front end 11 with the center and rear portions being of a relatively common diameter. The toothpick as formed has a central hollow core 12 running the entire length of the appliance. The front portion 11 tapers forwardly in a spiral a layer at a time until only a single rolled layer remains defining the frontmost portion of hollow core 12. The central core 12 becomes larger at the rear of the toothpick in that it is enlarged spirally a layer at a time until only the outer layer of the toothpick remains defining the rear-most portion of hollow core 12.

The shape of the toothpick 10 and its corresponding front end 11 and hollow core 12 are determined by the shape of the material from which it is formed and the manner in which it is rolled.

Figures 3, 4:
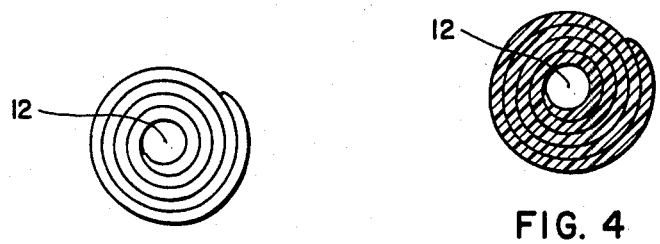
FIG. 3 is an end view of a toothpick as illustrated in either of FIGS. 1 and 2.
FIG. 4 is a cross-sectional view of a toothpick as taken along lines 4—4 of FIGS. 1 and 2.

FIGS. 3 and 4 show the layered forward and central cross-sectional portions of a toothpick rolled from a unitary piece of plastic.

Figures 5A, 5B, 5C, 5D, 5E:
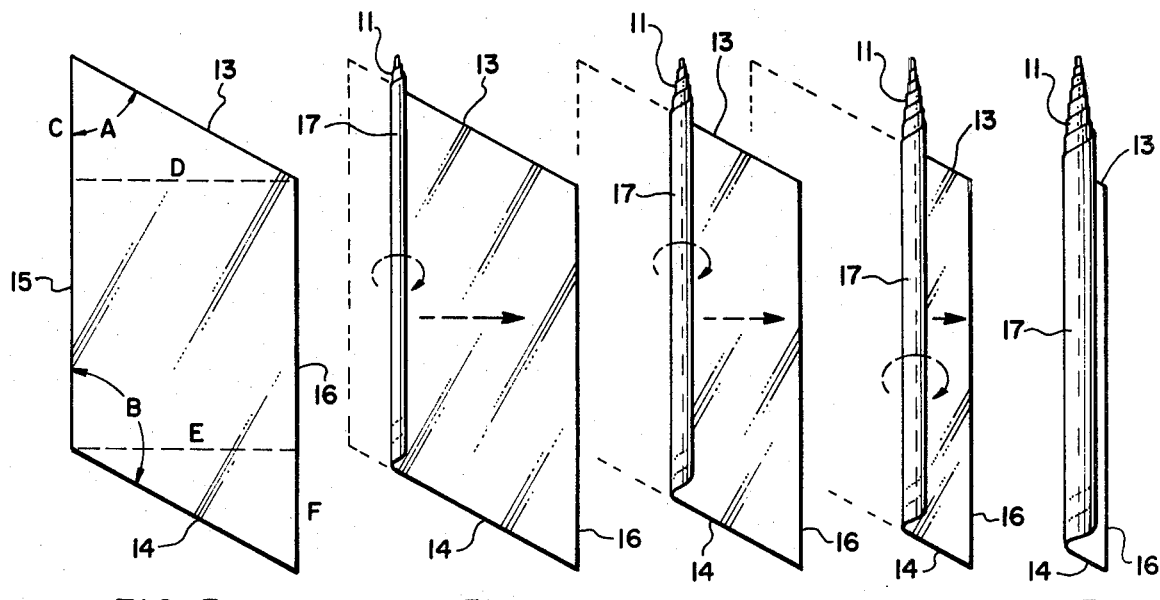
FIGS. 5a to 5e are a sequential illustration of a sheet of plastic being rolled to form the toothpick of FIG. 1.

The toothpick of FIG. 1 is formed from a piece of material having the general shape of a parallelogram having two acute and two obtuse angles as shown in FIG. 5a. The length of the parallelogram is preferably about two times its width but may vary from about one to three times the width. The dimensions are not critical as long as the toothpick is functional for its intended use. Preferably the acute angles A are between about 40 to 80 degrees and the obtuse angles B are between 100 and 140 degrees with angles of 60 and 120 being about optimal. However, the invention is not to be limited to any particular set of angles as long as the resulting toothpick formed therefrom is functional. As illustrated in FIGS. 5a to 5e, the parallelogram shaped plastic sheet consists of a top edge 13, a bottom edge 14, a forward edge 15 and a backward edge 16. Acute angle A is bounded by the top and forward edges and by the bottom and backward edges. Obtuse angle B is bounded by the bottom and the forward edges and by the top and backward edges. The toothpicks are manufactured by tightly curling the forward edge 15 into a column 17 parallel to the backward edge 16 and rolling the column 17 backwardly upon itself as illustrated in FIGS. 5b, c, d and e to form a finished product 10. The first curl of forward edge 15 defines hollow core 12 and the area in FIG. 5a bounded by lines 13 C and D comprise the tapered front end 11 of toothpick 10. Edge 13 thus becomes the tapered spiraling edge of the front end 11. The spiraling angle will depend upon angle A. The smaller angle A becomes the greater the spiraling of edge 13 becomes and the fewer layers there will be in front end 11.

The area bounded by lines 14 E and F define the tail portion of the toothpick where hollow core 12 tapers outwardly in size along the spiraling ridge form from edge 14.

The toothpick may be made of any thin sheet of resinous material which can be tightly rolled and be made to retain its rolled configuration. Polyolefins such as polypropylene and polyethylene are particularly suitable. However, other polymeric sheets or films such as polyvinyl chloride and polytetrafluoroethylene may also be used. The type of plastic material need meet only two essential requirements. One, it must be capable of maintaining its curled configuration and, second, it must be non-toxic.

Plastic sheets having the desired parallelogram shape may be hand rolled about thin wires and held in a rolled position until there is no tendency to unroll at which time the wires are removed. The rolled sheets may be heat treated and cooled in the rolled position to improve the ability of the plastic sheet to remain in a rolled position. In the alternative, a solid slab of plastic may be machined with a properly configured router to cut and roll appropriately shaped toothpicks as is more completely disclosed and claimed in copending patent application, Ser. No. 159,484 filed of even date herewith. Preferably the film sheets, hand rolled or machine cut and rolled will have a sheet thickness of from about 1.0 to 5.0 mils and a rolled diameter of about 40 to 80 mils. Preferably the toothpick will be about the same length as a conventional wooden toothpick, i.e., about 2 to 2½ inches with the tapered front end 11 taking up about 20 to 35 percent of the overall length.

A second embodiment of the invention is shown in FIGS. 2, 3, 4 and 6a to 6e.

As depicted in FIGS. 2 and 6a to 6e, the second embodiment is a differently shaped toothpick 20 consisting of a single sheet of flexible plastic material having a relatively pointed front end 21 which has a small central aperture 22 or hollow core which extends the entire length of the appliance 20. The toothpick is in the form of a layered, forwardly and backwardly extending, spiral with the greatest amount of layers occurring in a central portion 23. The front portion 21 tapers forwardly in a spiral a layer at a time until only a single rolled layer remains defining the central core 22. The rear portion 24 extends rearwardly and decreases in spirals a layer at a time until a single rolled layer remains which also defines the rear opening into the central core. The rear portion 24 has a larger opening than the front end since it has a diameter defined by several layers of rolled material located at the forward portion.

Toothpick 20 also has a shape which is determined by the configuration of the material from which it is formed. FIGS. 3 and 4 are similar to both toothpicks 10 and 20 in that both have spirally tapered front ends and a cross-section consisting of several layers of a unitary plastic material which has been rolled.

Toothpick 20 is formed from a rectangular piece of material as shown in FIG. 6a having a width that is approximately one-half of its length. This, however, is not a rigid requirement. For example, a square sheet of material can be used as can a sheet wherein the length is up to three times the width. In other words, the invention is not to be limited to any particular ratios of length to width as long as the resulting toothpick formed therefrom is functional.

As illustrated in FIGS. 6a through 6e, the rectangular shaped plastic sheet has an upper edge 25, a bottom edge 26, a front edge 27 and a back edge 28. The toothpicks are manufactured by tightly curling the corner bounded by top edge 25 and front edge 27 angularly into a column 29 as shown in FIG. 6b. The angle G may vary from about 20 to 40 degrees from the longitudinal plane of the material with angles in the neighborhood of about 30 degrees being preferred. Column 29 is tightly rolled with particular emphasis being placed on maintaining as tight a roll as possible on the end portion of column 29 consisting of forward edge 27. This is because, as shown in FIG. 6c, d and e, the forward end 21 of the toothpick 20 is formed from the corner of the material defined by the juncture of forward edge 27 and bottom edge 26.

Figure 2:
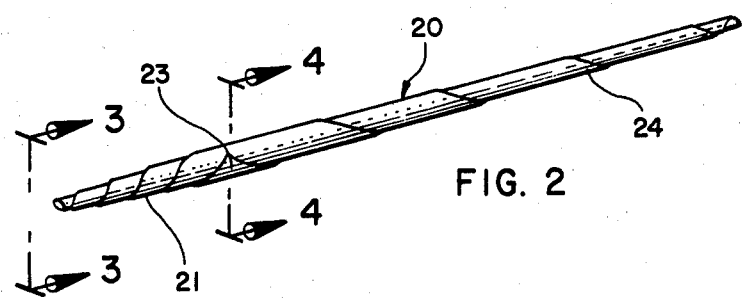
FIG. 2 is an enlarged perspective view of a second embodiment of a layered toothpick having both ends tapered.

As shown in FIG. 2 and FIG. 6c, d and e, the final wrap in forming the toothpick 20 is at the corner of the material resulting from the juncture of rear edge 29 and bottom edge 26. This final wrap occurs just forward of the central portion 23 of the toothpick 20. The result is that the leading edge at the rear portion 24 of the toothpick has a greater lineal spiral and that the leading edge of the tapered portion of the forward end of the toothpick has a greater lateral spiral.

Other than having both ends tapered, toothpick 20 is of generally the same size as toothpick 10 and is made of the same material. The method of manufacture may be similar in that rectangular sheets of material may be handrolled using small wires and the like to assist in the rolling procedure. The columns or toothpicks thus rolled may be held in this position until the plastic material conforms to the rolled shape and has no tendency to unravel. It is also possible to manufacture toothpick 20 from a solid sheet of material using a spiral router as more specifically described in copending application, Ser. No. 159,484 filed of even date herewith.

It is evident from FIGS. 1 and 2 that the tapered spiraling layers forming the forward and rearward portions of the toothpicks have leading edges or ridges such that when any tapered end of the appliance is pushed between the teeth or against a gum surface the cleaning action extends beyond the extreme end of the toothpick to the spiraling ridges which also serve as cleaning edges to remove plaque or other materials from the teeth and stimulate gingival surfaces. Pressure against these ridges causes a spring-like action to the toothpick wherein the coils tend to expand to a larger diameter.

FIG. 11 shows how a toothpick 10 of the present invention may be bent at the forward end 11 to be inserted between a user's teeth 30 and 31 at an angle which would not be possible with a rigid toothpick. Once the tip of forward end 11 of toothpick 10 has been inserted into a crevice between teeth 30 and 31 or 32 and 33 as shown, in either of FIGS. 11 and 12, the application of additional pressure to the toothpick 10 will cause forward end 11 to be deformed and assume the shape of the crevice as shown in FIG. 12. Also, because of the flexibility of the toothpick, the application of pressure will cause the toothpick to follow the path of least resistance. This means that the toothpick of this inventor may bend or flex into areas around the base of a tooth or extend into close areas between teeth that are impossible to reach with a conventional rigid toothpick.

The toothpicks easily conform to the shape of interproximal areas between teeth with the leading ridges removing plaque and also stimulate intra-dental papilla. The texture of the toothpick is sufficiently soft that gingival tissues are not damaged. Rather, such tissues are stimulated. An additional advantage of the flexibility of the toothpicks is that if forced into the mouth by a sudden impact, i.e., a child falling, the appliance will collapse instead of gouging into tissues in the oral cavity.

When the back end 24 of toothpick 20 is partially uncurled, the hollow core 22 will expand to fit about a tooth causing the layered material to extend into the gingival crevice for labial and lingual subcus stimulation.

Because of the thinness of the individual layers, the toothpicks of this invention become especially useful in cleaning fixed artificial dental appliances, i.e., pontic cleaning. By placing the appliance adjacent a pontic structure and applying pressure, the toothpick will follow the contour of the pontic shape. An ordinary toothpick is too thick and rigid to accomplish this result. Similarly the toothpicks are also useful in cleaning removable dentures without the necessity of first removing them from the mouth.

The hollow core 12 and 22 of the toothpicks serve as capillary tubes and may be used to remove blood or other liquids from specific locations within the oral cavity. The capillary action may also be utilized to carry breath fresheners or medicines to the oral cavity. For example, when a small packet containing toothpicks according to this invention is treated with a liquid breath freshener, the capillary action causes the hollow cores to be filled. When these treated toothpicks are subsequently used, the breath freshener may be rapidly sucked into the oral cavity or, with normal use, will slowly diffuse into the mouth of a user.

There are many modifications which may be made to the toothpicks to obtain various desired results. FIGS. 7, 8, 9 and 10 illustrate two of these modifications but the invention is not to be construed as being limited to these variations as others may also be apparent to those skilled in the art.

FIG. 7 shows a plastic sheet 34 similar to that shown in FIG. 5a wherein the top edge 35 is scored or notched to form small strips 36. When a toothpick 37 as shown in FIG. 8 is formed, these strips 36 comprise the leading spiraling front edge of the tapered front end 38 of the toothpick. Upon the application of pressure, as by pushing the toothpick into a crevice between two teeth, the strips 36 bend outwardly forming bristles which brush the teeth and massage the gums as the toothpick is manipulated in and out of the crevice.

FIG. 9 is similar to FIG. 7 except the plastic sheet 39 is serrated at the top edge 40 instead of being scored to form strips. When sheet 39 is rolled to form a toothpick 41, the serrated edge becomes the tapered front portion 42 of the toothpick 41 as shown in FIG. 10. When the toothpick is used to clean the teeth of a user, the serrations are more effective in removing plaque or other materials than is a corresponding toothpick wherein the leading spiraling edge is not serrated.

While the above description is deemed to illustrate a preferred embodiment of the invention, the invention is not to be limited by the specific embodiments shown but is to include all equivalent embodiments and modifications encompassed by the appended claims.

I claim:

1. A toothpick for cleaning teeth and gingival stimulation comprising a thin sheet of flexible plastic material capable of maintaining a configuration that is tightly curled back upon itself and rolled to form a layered body having a hollow central core, said body having a pointed forwardly tapered front portion containing spiraling ridges formed from one side edge of the curled material and with each outer layer of plastic material forming the layered body being movable over an inner layer.

2. Toothpick according to claim 1 wherein the forwardmost point of the tapered front portion consists of a single curl of flexible material which defines the minimum and forward diameter of the hollow central core.

3. A toothpick according to claim 2 wherein the diameter of the hollow central core at the rear of the body is larger than at the front.

4. A toothpick according to claim 3 wherein the flexible material is in the shape of a parallelogram having two acute angles and wherein the material is tightly curled along one side and rolled in a parallel relationship from one side to the opposing side.

5. A toothpick according to claim 4 wherein the acute angles of the material are between about 40 and 80 degrees and the obtuse angles of the material are between about 100 and 140 degrees.

6. A toothpick according to claim 5 wherein the acute angles are about 60 degrees and the obtuse angles are about 120 degrees.

7. A toothpick according to claim 5 wherein the material has a length that is from about one to three times the width.

8. A toothpick according to claim 7 wherein the length of the material is about twice the width.

9. A toothpick according to claim 7 wherein the material has a thickness of from about 1 to 5 mils.

10. A toothpick according to claim 3 wherein the flexible material is generally rectangular in shape and wherein the material is angularly curled at a predetermined angle beginning at one corner and rolled at such an angle until all of the material has been rolled forming a body having a central portion and front and rear tapered portions having tapered spiraling ridges formed from the curling of the material.

11. A toothpick according to claim 10 wherein the angle at which the material is curled varies about 20 to 40 degrees from the longitudinal plane of the rectangular sheet of material from which the toothpick is made.

12. A toothpick according to claim 11 wherein the angle at which the material is curled is about 30 degrees from the longitudinal plane of the rectangular sheet of material from which the toothpick is made.

13. A toothpick according to claim 11 wherein the material has a length that is from about one to three times the width.

14. A toothpick according to claim 13 wherein the length of the material is about twice the width.

15. A toothpick according to claim 13 wherein the material has a thickness of from about 1 to 5 mils.

16. A toothpick according to claim 3 wherein the spiraling ridges are scored.

17. A toothpick according to claim 3 wherein the spiraling ridges are serrated.

* * * * *